United States Patent

Raspanti

Patent Number: 5,362,481
Date of Patent: Nov. 8, 1994

[54] BENZOFURAN DERIVATIVES AND THE USE THEREOF AS STABILIZERS AGAINST UV RADIATIONS

[75] Inventor: Giuseppe Raspanti, Bergamo, Italy

[73] Assignee: 3V Inc., Weehawken, N.J.

[21] Appl. No.: 102,801

[22] Filed: Aug. 6, 1993

[51] Int. Cl.$^5$ .................... C07D 307/81; A61K 7/42; A61K 7/44
[52] U.S. Cl. ........................ 424/59; 424/60; 514/469; 549/469
[58] Field of Search ................ 549/469; 514/469; 424/59, 60

[56] References Cited

U.S. PATENT DOCUMENTS 2,104,492 1/1938 Merkel et al. ..................... 424/59

OTHER PUBLICATIONS

Chamberlin et al., Pestic. Sci., vol. 11, pp. 526-532 (1980).
El-Kerdawy et al., Arch. Pharm. Chem., Sci. Ed. vol. 11, pp. 129-136 (1983).

*Primary Examiner*—Bernard Dentz
*Attorney, Agent, or Firm*—Griffin Butler Whisenhunt & Kurtossy

[57] ABSTRACT

Compounds of the general formula I

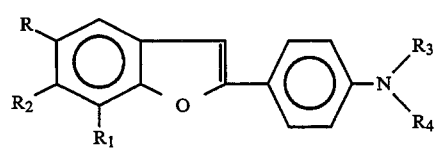

wherein R—$R_4$ are as defined in the description, have stabilizing activity against UV radiation and are useful in cosmetics and dermatology.

12 Claims, No Drawings

BENZOFURAN DERIVATIVES AND THE USE THEREOF AS STABILIZERS AGAINST UV RADIATIONS

The present invention relates to benzofuran derivatives and to the use thereof in cosmetics and dermatology.

Particularly, the present invention relates to compounds of the general formula I:

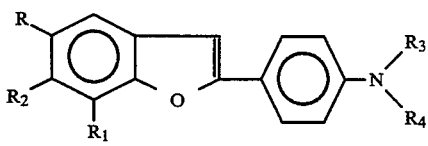

wherein R and $R_1$ are hydrogen or a $C_1-C_8$ straight or branched alkyl group, $R_2$ is hydrogen or a $C_1-C_4$ alkoxy group, $R_3$ is hydrogen or a $C_1-C_{18}$ straight or branched alkyl group, $R_4$ is a $C_1-C_8$ straight or branched alkyl group or a group of formula (II), (III), (IV) or (V)

$$-CO-R_5, \qquad \text{II}$$

$$-CO-NH-R_6, \qquad \text{III}$$

$$-COOR_7, \qquad \text{IV}$$

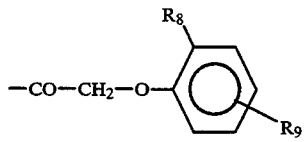 V wherein $R_5$ is a $C_2-C_{17}$ straight or branched alkyl group, $C_5-C_8$ cycloalkyl or $C_6-C_{12}$ aryl group, optionally substituted with $C_1-C_4$ alkyl groups, hydroxy, $C_1-C_{18}$ alkoxy, or a group of formula (VI)

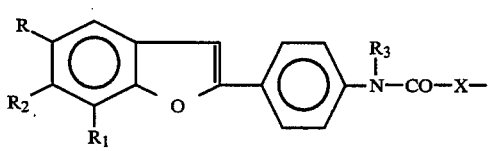 VI wherein R, $R_1$, $R_2$, $R_3$ have the above defined meanings and X can be a carbon-carbon single bond, $C_2-C_{10}$ alkylene, $C_5-C_8$ cycloalkylene or $C_6-C_{12}$ arylene, $R_6$ and $R_7$ are a $C_1-C_{18}$ straight or branched alkyl group or a $C_5-C_8$ cycloalkyl group, $R_8$ and $R_9$, which can be the same or different from each other, are hydrogen, $C_1-C_8$ straight or branched alkyl group, $C_1-C_{18}$ alkoxy, or a $-COOR_{10}$ group, wherein $R_{10}$ is $C_1-C_{18}$ straight or branched alkyl group.

Examples of straight or branched alkyl group are: methyl, ethyl, propyl, isopropyl, butyl, isobutyl, tertbutyl, hexyl, heptyl, 1-ethylpentyl, 4-methylhexyl, octyl, nonyl, 5-ethylheptyl, 6-methyloctyl, decyl, tetradecyl, 3-methyl-5-propyl-7-ethyldecyl, octadecyl.

Examples of $C_1-C_4$ alkoxy group are: methoxy, ethoxy, isopropoxy, tertbutoxy.

Examples of cycloalkyl group are: cyclopentyl, cyclohexyl, cycloheptyl, methylcyclopentyl, tertbutylcyclohexyl, methylcyclopentyl.

Examples of aryl group are: phenyl, biphenyl, naphthyl, o-, m-, p-hydroxyphenyl, 4-hydroxy-3,5-ditertbutylphenyl.

Examples of arylalkyl group are: benzyl, 1-phenylethyl 2-phenylpropyl, naphthylethyl.

Examples of groups of formula II are: propionyl, butirryl, pivaloyl, capriloyl, lauroyl, benzoyl, 4-phenyl-3,5-ditertbutylbenzoyl.

Examples of groups of formula III are methylcarbamoyl, propylcarbamoyl, heptylcarbamoyl, heptadecylcarbamoyl.

Examples of groups of formula IV are: carbomethoxy, carboethoxy, carboisopropoxy, carbotertbutoxy, carboheptyloxy, carbohexadeciloxy.

Examples of groups of formula V are: phenoxyacetyl, 2,3-xylyloxyacetyl, 5-methoxy-2-methylphenoxyacetyl, 2-carbomethoxyphenoxyacetyl.

Preferred compounds are those of formula Ia:

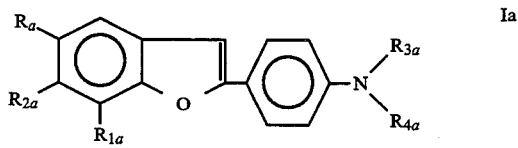 Ia wherein $R_a$ and $R_{1a}$ are hydrogen or $C_1-C_4$ straight or branched alkyl group, $R_{2a}$ is hydrogen or $C_1-C_4$ alkoxy group, $R_{3a}$ is hydrogen or $C_1-C_8$ straight or branched alkyl group, $R_{4a}$ is $C_1-C_8$ straight or branched alkyl group or a group of formula V as above defined or a group of formula IIa $$-CO-R_{5a} \qquad \text{IIa}$$

wherein $R_{5a}$ is $C_2-C_{17}$ straight or branched alkyl group, phenyl group, optionally substituted with $C_1-C_4$ alkyl group, $C_1-C_8$ alkoxy group; or a group of formula IVa, $$-COOR_{7a} \qquad \text{IVa}$$

wherein $R_{7a}$ is $C_1-C_8$ straight or branched alkyl group.

The following compounds are most preferred:
2-(p-N,N-dimethylaminophenyl)benzofuran;
2-(p-N,N-diethylaminophenyl)benzofuran;
2-(p-N-butylaminophenyl)benzofuran;
2-(p-N-ethylaminophenyl)benzofuran;
2-(p-N-octylaminophenyl)benzofuran;
2-[p-(N-pivaloylamino)phenyl]benzofuran;
2-[p-(N-octanoylamino)phenyl]benzofuran;
2-[p-(N-dodecanoylamino)phenyl]benzofuran;
2-[p-(N-pivaloyl-N-octylamino)phenyl]benzofuran;
2-{p-[N-(4-hydroxy-3,5-ditertbutyl)benzoylamino]phenyl}benzofuran;
2-{p-[N-(2-ethylhexanoyl)amino]phenyl}benzofuran;
2-{p-[N-(2-carbomethoxy)phenoxyacetylamino]phenyl}benzofuran;
2-{p-[N-(p-tertbutylbenzoyl)amino]phenyl}benzofuran;
2-{p-[N-(carbohexadecyloxy)amino]phenyl}benzofuran.

Ultraviolet radiations of sunlight are known to exert a damaging action on skin tissue.

In fact, the prolonged exposure to sunlight is considered to be the main cause in the development degenerative processes and of some skin tumours.

Ultraviolet radiation is also known to cause degradation of synthetic polymers.

By using particular compounds, the so-called sunscreens, which are capable of absorbing the UV part of solar radiation, the damaging effects and the aging of the skin and polymer materials can be prevented or, at least, slowed down.

A number of substances have been studied and tested as protecting agents, and an extensive patent literature exists on this subject, in which compounds belonging to different chemical classes are proposed, which are capable of absorbing in the ultraviolet region, particularly the radiation from 290 to 360 nm.

The radiation from 290 to 320 nm (named UV-B) causes erythema to form, whereas the one from 320 to 400 nm (named UV-A) is responsible for skin sun tan.

Sunscreens absorbing in the UV-B region are widely used as protecting agents against sunburns; whereas the use of sunscreens to shield skin from UV-A radiations was unknown until some time ago, except for some cases of particular therapies.

However, recent researches evidenced that the continued and intensive UV-A radiation can also cause remarkable skin damages, particularly to persons having a very sensitive, delicate skin.

Only a few of the compounds proposed up to now as sunscreens proved suitable to be for the practical application, among these, p-methoxy-cinnamic acid and p-dimethylaminobenzoic acid esters, benzotriazoles, hydroxybenzophenones and dibenzoylmethane derivatives.

The common drawback of all these compounds is the low power thereof to absorb the radiation from 290 to 360 nm. Therefore, it is necessary to use relatively large amounts thereof in cosmetic compositions to obtain an optimum light-protecting capability, accordingly the use thereof in practice can give rise to problems from the toxicologic and economic point of view.

In DOS 3 205 398 Patent Publication, s-triazine derivatives are disclosed, obtained by reacting trichlorotriazine with p-aminobenzoic acid esters, which derivatives have an absorption power much higher than those of the above cited chemical classes. However, these compounds only absorb in a restricted UV-B region and they are not suitable to exert a complete protecting action.

An optimum UV absorber should have the following characteristics:

1) high specific extinction to allow a low dosage and accordingly cost-savings and a minimum toxicological risk;
2) light stability;
3) heat stability;
4) good solubility, emulsifiability or dispersibility in base substances commonly used for the preparation of cosmetic formulations;
5) negligible toxicity;
6) colour and odour which are compatible with the envisaged uses;
7) comparatively high molecular weight, therefore with a lower probability of absorption by the skin and a higher safety from the toxicological point of view;
8) compatibility with the various substances generally used in dermatological formulations.

It has surprisingly been found that the compounds of the present invention absorb very effectively UV radiations; therefore small amounts of these compounds are sufficient to obtain cosmetic formulations having a high SPF (sun protection factor).

Moreover, compounds of formula (I) have a very wide absorption, which is not localized to a very restricted area of UV spectrum. In fact, the compounds of the invention, depending on the $R_3$ and $R_4$ substituents, show absorption peaks at the same time in both the UV-B region and the UV-A region thus exerting their protecting activity from all the radiations comprised from 290 to 360 nm.

Therefore, a further object of the invention resides in the use of the compounds of formula (I) as sunscreens and light stabilisers, thanks to the capability thereof of exerting a surprising protection activity on the skin from the noxious component of sunlight radiation.

The compounds of the invention are also valuable for use in light stabilization of synthetic polymers, in order to prevent light degradations and alterations.

The compounds of the present invention can be prepared by reacting compounds of formula (VII)

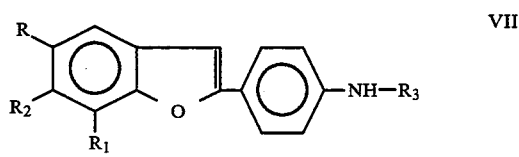

wherein R, $R_1$, $R_2$ and $R_3$ are as above defined, with a compound of formula VIII–XII

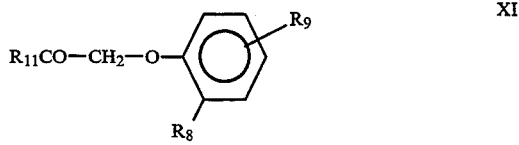

wherein $R_5$, $R_6$, $R_7$, $R_8$, $R_9$ and X have the above mentioned meanings and $R_{11}$ is a chlorine atom or a group —$OCH_3$, —$OC_2H_5$.

From 2-(p-nitrophenyl)benzofuran, optionally substituted, by catalytic reduction with hydrogen or with stannous chloride and hydrochloric acid, as described in Ann. Chim. 53, 1751–1760 (1963), 2-(p-aminophenyl)-benzofuran is obtained, from which then, by conventional alkylation with alkyl sulfates or alkyl halides or by reductive alkylation with aldehydes or ketones, the compounds of formula VII, wherein $R_3$ is alkyl, or, by changing the stoichiometric ratios between the reactants, compounds of formula I, wherein $R_3$ and $R_4$ are $C_1$–$C_{18}$ alkyl, are obtained.

The reactions between the compounds of formula VII and the compounds of formula VIII–XII, to obtain the compounds of formula I, according to the invention, are carried out in inert solvents, such as for example acetonitrile; ketones, such as acetone, methyl ethyl ketone; ethers such as diethyl ether, diisopropyl ether, tetrahydrofuran, dioxane; aliphatic cycloaliphatic or aromatic hydrocarbons such as pentane, hexane, cyclohexane, benzene, toluene, xylene or mixtures thereof.

Compounds wherein $R_{11}$ is a chlorine atom are preferred. Tertiary amines, such as for example trimethylamine, dimethylaniline, diethylaniline, or alkali or alkaline-earth metal hydroxides, alkali metal carbonates or hydrogencarbonates are used as acid acceptors.

Reaction temperature can range from 0° C. to 150° C. depending on the reactants VIII–XII and the solvents to be used.

The obtained compounds are recovered and purified by means of well known methods.

According to one of the preferred embodiments of the invention, the compositions containing the compounds of formula (I) as active ingredients are topically applied on the skin to protect it from the damaging effects of sunlight radiations.

A further object of the present invention consists in the use of the compounds of formula I for the preparation of cosmetic and dermatological compositions useful for the protect ion of the skin against sun radiations.

The compounds according to the present invention can be added, of course also in combination with other stabilizers, to the cosmetic and dermatological compositions as well as to synthetic polymers, generally in amounts ranging from 0.05 to 15%, preferably from 0.1 to 10% by weight of the polymer or cosmetic composition.

The cosmetic compositions of the present invention can be of various kinds, such as for example, ointments, creams, lotions, emulsions, sun milk, lipsticks, sprays. Said compositions can be prepared by means of conventional techniques which are well known to the man skilled in the art, such as those described in "Remington's Pharmaceutical Sciences Handbook", XVII Ed.; Mack Pub.; N.Y., U.S.A.

The compounds of formula (I) are added either to protect the formulations themselves, for example to prevent undesired discolourations, or to protect the skin treated with the formulation from the damaging action of UV-A and UV-B radiations, which causes erythema and accelerates the ageing of the skin making it prematurely dry, wrinkled or squamous.

The following examples illustrate the invention.

EXAMPLE 1

21 g of sodium hydrogencarbonate and 50 g of dimethyl sulfate were added to 21 g of 2-(p-aminophenyl)-benzofuran dissolved into 150 ml of methoxyethanol.

The reaction mixture was heated at 60°–70° C. and stirred for 2 hours.

After cooling down to 20° C., the reaction mixture was poured into 300 ml of water and the formed precipitate was filtered, washed with water, dried and recrystallized form isopropanol.

19 g of 2-(p-N,N-dimethylaminophenyl)benzofuran, m.p. 178°–181° C. and E' (MeOH) of 1964 at 322 nm, were obtained.

EXAMPLE 2

By operating as in Example 1, but using diethyl sulfate, the corresponding 2-(p-N,N-diethylaminophenyl)-benzofuran, m.p. 117°–119° C. and E' (MeOH) of 1680 at 337 nm, was obtained.

EXAMPLE 3

30 g of butyl bromide and 27.6 g of potassium carbonate were added to 42 g of 2-(p-aminophenyl)benzofuran dissolved into 200 ml of dimethyl formamide.

The reaction mixture was heated up to 130° C. and stirred for 6 hours, then cooled and poured into water.

The formed precipitate was filtered, washed, dried and crystallized from methanol.

28 g of 2-(p-N-butylaminophenyl)benzofuran, m.p. 113°–115° C. were obtained.

EXAMPLE 4

By operating as in Example 3, but using diethyl sulfate, the corresponding 2-(p-N-ethylaminophenyl)benzofuran, m.p. 126°–128° C., was obtained.

EXAMPLE 5

By operating as in Example 3, but using octyl bromide, the corresponding 2-(p-N-octylaminophenyl)benzofuran, m.p. 87°–90° C., was obtained.

EXAMPLE 6

7.2 g of pivaloyl chloride were slowly added to a mixture of 13.2 g of 2-(p-aminophenyl)benzofuran and 5.5 g of sodium carbonate 100 ml of acetone, keeping the temperature between 20° and 30° C., then the reaction mixture was heated up to 50° C. and stirred for further 0.5 hour. The reaction mixture was poured into 200 ml water.

The formed precipitate was filtered, washed, dried and crystallized from toluene.

A whitish substance with the formula, m.p. and E' as shown in Table 1 was obtained.

EXAMPLES 7–14

By operating as in Example 6, but using other acyl chlorides and compounds of formula VII, the compounds listed in Table 1 were obtained, wherein R, $R_1$ and $R_2$ are hydrogen.

TABLE 1

XIII

| Example | $R_3$ | $R_{12}$ | MP °C. | E' | nm |
|---|---|---|---|---|---|
| 6 | H | $(CH_3)_3-C-$ | 228–231 | 1311 | 306 |
|   |   |   |   | 1508 | 317 |
|   |   |   |   | 922 | 332 |
| 7 | H | $C_7H_{15}$ | 198–201 | 1150 | 306 |
|   |   |   |   | 1333 | 318 |
|   |   |   |   | 848 | 332 |
| 8 | H | $C_{11}H_{23}$ | 186–188 | 980 | 306 |
|   |   |   |   | 1172 | 316 |
|   |   |   |   | 737 | 333 |
| 9 | $C_8H_{17}$ | $(CH_3)_3-C-$ | 72–74 | 991 | 309 |
|   |   |   |   | 826 | 321 |
| 10 | H | 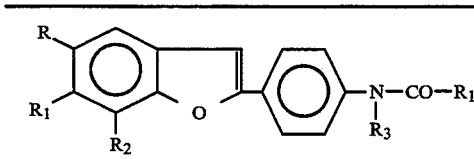 | >260 | 1206 | 324 |
| 11 | H | $C_4H_9-CH-$<br>\|<br>$C_2H_5$ | 218–220 | 1145 | 306 |
|   |   |   |   | 1372 | 318 |
|   |   |   |   | 858 | 334 |
| 12 | H | 2-(COOCH_3)-C_6H_4-O-CH_2- | 154–157 | 1256 | 301 |
|   |   |   |   | 1239 | 318 |
|   |   |   |   | 782 | 333 |

TABLE 1-continued

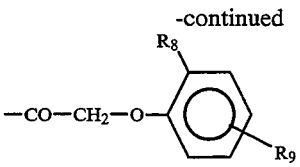

XIII

| Example | R$_3$ | R$_{12}$ | MP °C. | E' | nm |
|---|---|---|---|---|---|
| 13 | H | 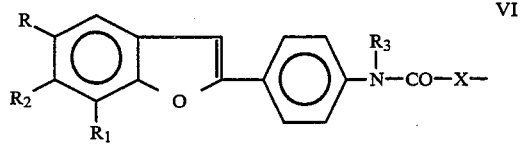 | 222–224 | 1295 | 324 |
| 14 | H | C$_{16}$H$_{33}$—O— | 131–133 | 1049<br>616 | 314<br>330 |

EXAMPLE 15

By operating as described in Example 16, from 2-[p-(N-octyl)aminophenyl]benzofurane and oxalyl dichloride, the compound of formula XIV, m.p. 112°–115° C. and E'-1010 at 315 nm and 1000 at 325 nm was obtained.

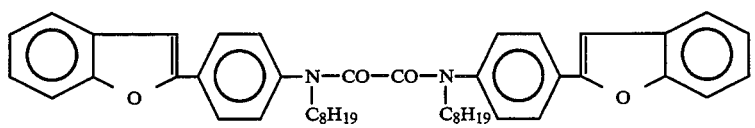

XIV

EXAMPLE 16

Preparation of a Sun Cream

A mixture consisting of 10 g of cyclodimeticone/-dimeticone copolymer (Dow Corning Q 2-3223), 10 g of cyclometicone (Dow Corning 344), 0.5 g of polysorbate 20 (Tween 20) and 2 g of the compound of Example 6 is prepared.

This mixture is added to a previously prepared solution of 0.2 g of 1,1'-methylene-bis-3-(3'-hydroxymethyl-2,4-dioxy-imidazolidinyl)urea, 0.05 g of methyl paraben and 77.25 g of water.

I claim:

1. Compounds of the formula (I)

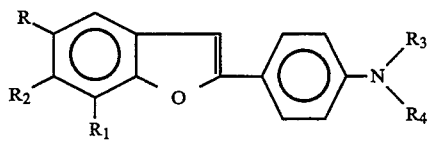

I wherein R and R$_1$ are hydrogen or a C$_1$-C$_8$ straight or branched alkyl group, R$_2$ is hydrogen or a C$_1$-C$_4$ alkoxy group, R$_3$ is hydrogen or a C$_1$-C$_{18}$ straight or branched alkyl group, R$_4$ is a group of formula (II), (III), (IV) or (V)

—CO—R$_5$,  II

—CO—NH—R$_6$,  III

—COOR$_7$,  IV

—CO—CH$_2$—O—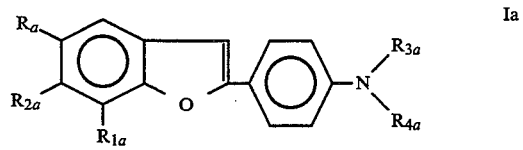  V wherein R$_5$ is a C$_2$-C$_{17}$ straight or branched alkyl group, C$_5$-C$_8$ cycloalkyl or C$_6$-C$_{12}$ aryl group, optionally substituted with C$_1$-C$_4$ alkyl groups, hydroxy, C$_1$-C$_{18}$ alkoxy, or a group of formula (VI)

VI wherein R, R$_1$, R$_2$, R$_3$ have the above defined meanings and X can be a carbon-carbon single bond, C$_2$-C$_{10}$ alkylene, C$_5$-C$_8$ cycloalkylene or C$_6$-C$_{12}$ arylene, R$_6$ and R$_7$ are a C$_1$-C$_{18}$ straight or branched alkyl group or a C$_5$-C$_8$ cycloalkyl group, R$_8$ and R$_9$, which can be the same or different from each other, are hydrogen, C$_1$-C$_8$ straight or branched alkyl group, C$_1$-C$_{18}$ alkoxy, or a —COOR$_{10}$ group, wherein R$_{10}$ is C$_1$-C$_{18}$ straight or branched alkyl group.

2. A compound according to claim 1, having the following formula Ia

Ia wherein R$_a$ and R$_{1a}$ are hydrogen or C$_1$-C$_4$ straight or branched alkyl group,
R$_{2a}$ is hydrogen or C$_1$-C$_4$ alkoxy group,
R$_{3a}$ is hydrogen or C$_1$-C$_8$ straight or branched alkyl group,
R$_{4a}$ is a group of formula V as above defined or a group of formula IIa —CO—R$_{5a}$  IIa wherein R$_{5a}$ is C$_2$-C$_{17}$ straight or branched alkyl group, phenyl group, optionally substituted with C$_1$-C$_4$ alkyl group, C$_1$-C$_8$ alkoxy group; or a group of formula IVa, —COOR$_{7a}$  IVa wherein R$_{7a}$ is C$_1$-C$_8$ straight or branched alkyl group.

3. A compound according to claim 1, selected from the group consisting of:
2-[p-(N-pivaloylamino)phenyl]benzofuran;
2-[p-(N-octanoylamino)phenyl]benzofuran;
2-[p-(N-dodecanoylamino)phenyl]benzofuran;

2-[p-(N-pivaloyl-N-octylamino)phenyl]benzofuran;
2-{p-[N-(4-hydroxy-3,5-ditertbutyl)benzoylamino]-phenyl}benzofuran;
2-{p-[N-(2-ethylhexanoyl)amino]phenyl}benzofuran;
2-{p-[N-(2-carbomethoxy)phenoxyacetylamino]-phenyl}benzofuran;
2-{p-[N-(p-tertbutylbenzoyl)amino]phenyl}benzofuran;
2-{p-[N-(carbohexadecyloxy)amino]phenyl}benzofuran.

4. Cosmetic and dermatological compositions comprising an admixture of a sunscreening or light stabilization effective amount of at least one compound of claim 1 and a cosmetically or dermatologically acceptable carrier.

5. The composition of claim 4, wherein the compound is contained in the composition in an amount of between about 0.05 and 15 w/w % of the composition.

6. The composition of claim 5, wherein the amount of the compound is between about 0.1 and 10 w/w % of the composition.

7. The composition of claim 4, wherein the composition contains an excipient.

8. The composition of claim 4 combined with an additional sunscreen composition.

9. Cosmetic and dermatological compositions according to claim 4 in the form of ointments, creams, lotions, emulsions, lipsticks, and sprays.

10. A method of protecting the skin from sunlight radiation consisting in topically applying on the skin a cosmetic and dermatological composition according to claim 4.

11. A method of stabilizing a cosmetic and dermatological composition, comprising adding at least one compound according to claim 1 to said composition in an amount ranging from 0.05 to 15% by weight of the composition.

12. A method of stabilizing a cosmetic and dermatological composition, comprising adding at least one compound according to claim 1 to said composition in an amount ranging from 0.1 to 10% by weight of the composition.

* * * * *